US009848602B2

(12) United States Patent
Tietjen et al.

(10) Patent No.: US 9,848,602 B2
(45) Date of Patent: Dec. 26, 2017

(54) USE OF PROTHIOCONAZOLE TO INDUCE HOST DEFENCE RESPONSES

(71) Applicant: BAYER CROPSCIENCE AKTIENGESELLSCHAFT, Monheim (DE)

(72) Inventors: Klaus Tietjen, Langenfeld (DE); Anne Suty-Heinze, Langenfeld (DE); Andreas Goertz, Gold River, CA (US); Martin Kaussmann, Sacramento, CA (US); Sascha Gille, Hofheim (DE); Thomas Knobloch, Chatillon (FR)

(73) Assignee: BAYER CROPSCIENCE AKTIENGESELLSCHAFT, Monheim (DE)

( * ) Notice: Subject to any disclaimer, the term of this patent is extended or adjusted under 35 U.S.C. 154(b) by 0 days.

(21) Appl. No.: 14/766,463

(22) PCT Filed: Feb. 17, 2014

(86) PCT No.: PCT/EP2014/052986
§ 371 (c)(1),
(2) Date: Aug. 7, 2015

(87) PCT Pub. No.: WO2014/128069
PCT Pub. Date: Aug. 28, 2014

(65) Prior Publication Data
US 2015/0373975 A1  Dec. 31, 2015

(30) Foreign Application Priority Data

Feb. 19, 2013  (EP) .................................... 13155868

(51) Int. Cl.
*A01N 25/00* (2006.01)
*A01N 43/653* (2006.01)

(52) U.S. Cl.
CPC .................................. *A01N 43/653* (2013.01)

(58) Field of Classification Search
None
See application file for complete search history.

(56) References Cited

U.S. PATENT DOCUMENTS

| 5,789,430 | A | 8/1998 | Jautelat et al. | |
| 5,859,039 | A | 1/1999 | Jautelat et al. | |
| 8,044,036 | B2 * | 10/2011 | Suty-Heinze | A01N 55/00 |
| | | | | 504/100 |
| 8,614,168 | B2 | 12/2013 | Dittgen et al. | |
| 8,658,564 | B2 * | 2/2014 | Suty-Heinze | A01N 37/46 |
| | | | | 504/100 |

FOREIGN PATENT DOCUMENTS

| WO | 9616048 A1 | 5/1996 |
| WO | 2010015337 A2 | 2/2010 |
| WO | WO 2010/015337 | * 2/2010 |

OTHER PUBLICATIONS

Walters et al. (Controlling crop diseases using induced resistance: challenges for the future, Journal of Experimental Botany,vol. 64, No. 5, Feb. 5, 2013 (Feb. 5, 2013), pp. 1263-1280.*
International Search Report and Written Opinion from Corresponding PCT/EP2014/052986, dated Apr. 16, 2014.
Abreu, "Salicylic acid may be involved in the regulation of drought-induced leaf senescence in perennials: A case study in field-grown Salvia officinalis L. plants", ELSEVIER, ScienceDirect, Departament de Biologia Vegetal, Universitat de Barcelona, Facultat de Biologia, Barcelona, Spain, Environmental and Experimental Botany 64 (2008) pp. 105-112.
Ashraf et al., "The Physiological, Biochemical and Molecular Roles of Brassinosteroids and Salicylic Acid in Plant Processes and Salt Tolerance", Taylor & Francis, Critical Reviews in Plant Sciences, 29, pp. 162-190, 2010.
Berr et al., "Chromatin modification and remodelling: a regulatory landscape for the control of Arabidopsis defence responses upon pathogen attack", Blackwell Publishing Ltd, Cellular Microbiology, (2012)14(6), pp. 829-839.
Chen et al., "Proline induces calcium-mediated oxidative burst and salicylic acid signaling", Springer-Verlag, Amino Acids, 2011, 40: pp. 1473-1484.
Conrath, "Molecular aspects of defence priming", Plant Biochemistry & Molecular Biology Group, Department of Plant Physiology, RWTH Aachen University, Aachen, Germany, Trends in Plant Science, Oct. 2011, vol. 16, No. 10, pp. 524-531.
Dowen et al., "Widespread dynamic DNA methylation in response to biotic stress", PNAS | Published online Jun. 25, 2012, pp. E2183-E2191.
Hammerschmidt, "Systemic Acquired Resistance", Department of Plant Pathology, East Lansing, MI, Advances in Botanical Research, vol. 51, 2009, Elsevier Ltd., pp. 174-222.
Jaskiewicz et al., "Chromatin modification acts as a memory for systemic acquired resistance in the plant stress response", Department of Botany, and Department of Plant Physiology, Rheinisch-Westfä˝ lische Technische Hochschule Aachen University, Aachen, Germany, EMBO reports, European Molecular Biology Organization, vol. 12, No. 1, 2011, pp. 50-55.
Lissarre et al., "Cold-responsive gene regulation during cold acclimation in plants", Plant Signaling & Behavior, vol. 5, Issue 8, pp. 948-952, Aug. 2010; Landes Bioscience.
Luna et al., "Next-Generation Systemic Acquired Resistance", Plant Physiology, Feb. 2012, vol. 158, pp. 844-853, www.plantphysiol. org, 2011, American Society of Plant Biologists.
Mathys et al., "Genome-wide characterization of ISR induced in Arabidopsis thaliana byTrichoderma hamatumT382 against Botrytis cinerea infection", frontiers in Plant Science, May 2012, vol. 3, Article 108, pp. 1-25.

(Continued)

*Primary Examiner* — Alton Pryor
(74) *Attorney, Agent, or Firm* — McBee Moore Woodward & Vanik IP, LLC

(57) ABSTRACT

The present invention relates to the novel use of Prothioconazole for inducing host defence responses in a plant. In particular, the present invention relates the use of Prothioconazole for inducing systemic acquired resistance (SAR) in a plant.

13 Claims, No Drawings

(56) References Cited

OTHER PUBLICATIONS

Mukherjee et al., "Potential of salicylic acid activity derived from stress-induced (water) Tomato against Meloidogyne incognita", Taylor & Francis, Archives of Phytopathology and Plant Protection vol. 45, No. 16, Oct. 2012, pp. 1909-1916.
Pieterse et al., "Molecular Mechanisms Involved in Induced Resistance Signaling in Arabidopsis", The Netherlands, 2006, pp. 188-194.
Pieterse et al., "Induced Systemic Resistance by Beneficial Microbes", Annu. Rev. Phytopathol., 2014, vol. 52, pp. 347-375.
Takahashi et al., "Beta-Cyanoalanine Synthase as a Molecular Marker or Induced Resistance by Fungal Glycoprotein Elicitor and Commercial Plant Activators", Biochemistry and Cell Biology, Phytopathology, vol. 96, No. 8, 2006, pp. 908-916.
Toquin et al., "Host Defense Inducers", Modern Crop Protection Compounds, Second Edition, Wiley-VCH Verlag GmbH & Co. KGaA, 2012, pp. 909-928.
Verhagen et al., "The Transcriptome of Rhizobacteria-Induced Systemic Resistance in Arabidopsis", MPMI vol. 17, No. 8, 2004, pp. 895-908. Publication No. M-2004-0609-01R, The American Phytopathological Society.
Rivas-San Vicente et al., "Salicylic acid beyond defence: its role in plant growth and development", Journal of Experimental Botany, vol. 62, No. 10, pp. 3321-3338, 2011.
Walters et al., "Controlling crop diseases using induced resistance: challenges for the future", Journal of Experimental Botany, vol. 64, No. 5, pp. 1263-1280, Advance Access publication Feb. 5, 2013.
Wu et al., "The Arabidopsis NPR1 Protein is a Receptor for the Plant Defense Hormone Salicylic Acid", Cell Press, Open Access, Cell Reports 1, pp. 639-647, Jun. 28, 2012, The Authors.
Zhang et al., "Extracellular pyridine nucleotides induce PR gene expression and disease resistance in Arabidopsis", The Plant Journal (2009) 57, pp. 302-312.
Schmelz et al., "Simultaneous analysis of phytohormones, phytotoxins, and volatile organic compounds in plants", PNAS, Sep. 2, 2003, vol. 100, No. 18, pp. 10552-10557.

* cited by examiner

USE OF PROTHIOCONAZOLE TO INDUCE HOST DEFENCE RESPONSES

CROSS REFERENCE TO RELATED APPLICATIONS

This application is a §371 National Stage Application of PCT/EP2014/052986, filed 17 Feb. 2014, which claims priority to EP 13155868.6, filed 19 Feb. 2013.

BACKGROUND

Field of the Invention

The present invention relates to the novel use of Prothioconazole for inducing host defence responses in a plant.

Description of Related Art

It is assumed that all plants have the intrinsic capacity to defend themselves against pathogen attacks. Plants can be induced to deploy enhanced defenses and this can be triggered by various stimuli and chemicals. In the natural environment, disease resistance reactions of plants can be induced by e.g. microorganisms, insects, or abiotic stresses like drought or heat. Numerous species of bacteria, fungi, pathogen-derived molecules, cell-wall components of fungi, peptides or plant extracts are commercialized as biological or natural control agents for crop diseases. These biotic factors can induce systemic acquired resistance (SAR) in plants (B. W. M. Verhagen et al., in Mol Plant Microbe Interact. (2004), vol. 17, pp. 895-908; H. Takahashi et al., in Phytopathology. (2006), vol. 96, pp. 908-916). Likewise synthetic chemical inducers of SAR are known (V. Toquin et al. in 'Modern Crop Protectioon Compounds', W. Krämer et al. (eds), 2012, Vol. 2, pp. 909-928).

Induced resistance is often a systemic response with long lasting effects that confers a broad spectrum of resistance. It is regulated by a network of signaling pathways which involve endogenous phytohormones, in particular: salicylic acid (SA), jasmonic acid (JA) (Figure 1) and ethylene.

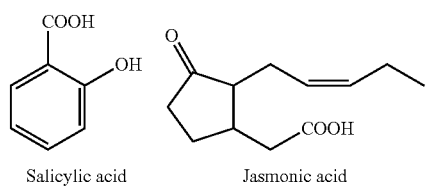

FIG. 1. Phytohormones

Salicylic acid          Jasmonic acid

The plant hormone salicylic acid (SA) is prominently involved in plant defense responses against biotic and abiotic stresses. Exogenous application of SA confers stress tolerance (Ashraf et al., in: Critical Reviews in Plant Sciences (2010), 29(3), 162-190; Rivas-San and Plasencia in: Journal of Experimental Botany (2011) 62(10), 3321-3338). SA-induced stress tolerance, which is systemic acquired resistance (SAR), is effective against a broad range of abiotic stresses as well as against fungal, bacterial, oomycetal, viral or even nematodal infection (Hammerschmidt in: Advances in Botanical Research (2009), 51 (Plant Innate Immunity), 173-222; Mukherjee et al. in: Archives of Phytopathology and Plant Protection (2012), 45(16), 1909-1916). Some host plant resistance inducing compounds in the fungicide market are mimics of SA, like e.g. acibenzolar-S-methyl (V. Toquin et al., in: 'Modern Crop Protectioon Compounds', W. Krämer et al. (eds), 2012, Vol. 2, pp. 909-928; Wu et al. in: Cell Reports (2012), 1(6), 639-647.).

Numerous abiotic and biotic stresses were found to increase SA levels as e.g. cold (Lissarre et al., in: Plant Signaling & Behavior (2010), 5(8), 948-952.), drought (Abreu and Munne-Bosch, in: Environmental and Experimental Botany (2008), 64(2), 105-112), the amino acid proline (Chen et al., in Amino Acids (2011), 40(5), 1473-1484), extracellular nucleotides (Zhang et al. in: Plant Journal (2009), 57(2), 302-312) or infection (Schmelz et al. in: Proceedings of the National Academy of Sciences of the United States of America (2003), 100(18), 10552-10557.). This means that stress itself can induce later stress resistance (SAR) via SA signaling. Accordingly to this induction of SA accumulation is sufficient to induce SAR in plants (M. Ashraf et al. in Critical Reviews in Plant Sciences (2010), 29(3), 162-190).

SA-mediated SAR is commonly distinguished from induced systemic resistance (ISR). ISR is in contrast to SAR and in reciprocal antagonism to salicylate signaling ascribed to jasmonate and ethylene signaling (Pieterse et al. in: Biology of Plant-Microbe Interactions (2006), 5, 188-194; Pieterse et al. in: Nature Chemical Biology (2009), 5(5), 308-316). However, a recent and more holistic interpretation of gene expression profiling data shows that SA is involved in establishment of ISR as well and SAR and ISR resemble each other closely (Mathys et al. in: Frontiers in Plant Science (2012), 3, 108. doi: 10.3389/fpls.2012.00108).

SA-induced SAR spreads throughout the plant. The effect of SA and SAR on plant gene expression persists throughout long times after SA induction or application. This effect is conceptionally described as priming (Conrath 2011 in: Trends in Plant Science (2011), 16(10), 524-531). The nature of priming is epigenetic chromatin modification on histone proteins and on DNA (Jaskiewicz et al. in: EMBO Reports (2011), 12(1), 50-55; Dowen et al. in: Proceedings of the National Academy of Sciences of the United States of America (2012), 109(32), E2183-E2191, 5E2183/1-5E2183/252). The effect is even inheritable (Luna et al. in: Plant Physiology (2012), 158(2), 844-853). The epigenetic SA effect resembles the plant defense response against biotic attack in general (Ben et al. in: Cellular Microbiology (2012) 14(6), 829-839).

SA accumulation can also induce a local acquired resistance, e.g. at plant parts which are particularly affected. Local acquired SA-induced resistance can then lead to a systemic acquired resistance by spreading throughout the plant.

SUMMARY

Surprisingly it has been found that the fungicide prothioconazole induces the accumulation of salicylic acid in plants and hence induces host defence responses in plants. Such induction of host defense responses by prothioconazole has been confirmed by gene expression analyses.

The present invention therefore relates to the novel use of the fungicide prothioconazole to induce host defence responses in plants.

DETAILED DESCRIPTION OF A PREFERRED EMBODIMENT

According to the present invention host defence responses are local or systemic defence responses of the plant, preferably systemic defence responses of the plant. A preferred host defence response according to the present invention is local or systemic acquired resistance (SAR), more preferably systemic acquired resistance (SAR). A particularly preferred host defence response according to the present invention is the accumulation of salicylic acid in the plant.

Therefore the present invention preferably relates to such a use of the fungicide Prothioconazole, wherein the treatment of the plant, plant parts or seeds induces local or systemic acquired resistance (SAR), in particular systemic acquired resistance (SAR).

By treating the plant, plant parts or seeds with the fungicide Prothioconazole the induced resistance can start as a local acquired resistance in the treated plant parts or seeds and result in a systemic acquired resistance (SAR) by spreading out throughout the whole plant. Since systemic acquired resistance (SAR) protects all, even newly grown parts of the plant, such systemic defence responses are preferred host defence responses according to the present invention.

According to a preferred embodiment the present invention relates to such a use of the fungicide Prothioconazole, wherein the treatment of the plant or plant parts induces local acquired resistance (SAR).

According to another preferred embodiment the present invention relates to such a use of the fungicide Prothioconazole, wherein the treatment of the plant or plant parts induces systemic acquired resistance (SAR).

According to another preferred embodiment the present invention relates to such a use of the fungicide Prothioconazole, wherein the treatment of the seeds induces systemic acquired resistance (SAR).

According to yet another preferred embodiment of the present invention the treatment of the plant, plant parts or seeds with Prothioconazole induces the accumulation of salicylic acid in the plant.

According to yet another preferred embodiment of the present invention the treatment of the plant, plant parts or seeds with Prothioconazole induces the expression of defense genes in the plant.

Prothioconazole (CAS Registry No. 178928-70-6), having the chemical name 2-[2-(1-chlorocyclopropyl)-3-(2-chlorophenyl)-2-hydroxypropyl]-1,2-dihydro-3H-1,2,4-triazole-3-thione (Compound A) and its manufacturing process is described in WO-A 96/16048.

Prothioconazole is well known [cf. The Pesticide Manual, Fifteenth Edition, C. D. S. Tomlin (Ed.), 2009, BCPC Publications] as fungicide. Triazole fungicides including the fungicide Prothioconazole are well known as sterol biosynthesis inhibitors, see FRAC classification (FRAC website http://www/frac.info/), in particular subgroup G1. It is in particular known that triaazole fungicides including the fungicide Prothioconazole are inhibitors of fungal sterol C14 demethylase cyp51, which is a cytochrome P450 monooxygenase. However, so far the use of triazole fungicides and in particular of the fungicide Prothioconazole as host defence inducer has never been reported before. The effect that Prothioconazole induces host defence responses and accumulation of salicylic acid is the more surprising since other triazole fungicides known as sterol biosynthesis inhibitors show a less substantial host defence response inducement and SA accumulation inducement.

The use of Prothioconazole according to the present invention increases the plant's resistance against phytopathogenic pathogens or pests, e.g. phytopathogenic fungi, oomycetes, bacteria, viruses, viroids, mycoplasma-like organisms, protozoa, insects, acari or nematodes.

The use of Prothioconazole according to the present invention in particular increases the plant resistance against pathogens of fungal and oomycetes diseases.

Non-limiting examples of such pathogens of fungal diseases include:

Diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fitliginea*; *Uncinula* species, for example *Uncinula necator*;

Diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite*, *P. triticina*, *P. graminis* or *P. striiformis*; *Uromyces* species, for example *Uromyces appendiculatus*;

Diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

Leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*, *Leptosphaeria nodorum*; *Magnaporthe* species, for example *Magnaporthe grisea*; *Microdochium* species, for example *Microdochium nivale*; *Mycosphaerella* species, for example *Mycosphaerella graminicola*, *M. arachidicola* and *M. fijiensis*; *Phaeosphaeria* species, for example *Phaeosphaeria nodorum*; *Pyrenophora* species, for example *Pyrenophora teres*, *Pyrenophora tritici repentis*; *Ramularia* species, for example *Ramularia collo-cygni*, *Ramularia areola*; *Rhynchosporium* species, for example *Rhynchosporium secalis*; *Septoria* species, for example *Septoria apii*, *Septoria lycopersii*; *Typhula* species, for example *Typhula incarnata*; *Venturia* species, for example *Venturia inaequalis*;

Root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

Ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladospori-

*oides; Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum*;

Diseases caused by smut fungi, for example *Sphacelotheca* species, for example *Sphacelotheca reiliana; Tilletia* species, for example *Tilletia caries, T. controversa; Urocystis* species, for example *Urocystis occulta; Ustilago* species, for example *Ustilago nuda, U. nuda tritici*;

Fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum; Verticilium* species, for example *Verticilium alboatrum*;

Seed and soilborne decay, mould, wilt, rot and damping-off diseases caused, for example, by *Alternaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes; Fusarium* species, caused for example by *Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma lingam; Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii; Septoria* species, caused for example by *Septoria nodorum; Typhula* species, caused for example by *Typhula incarnata; Verticillium* species, caused for example by *Verticillium dahliae*;

Cancers, galls and witches' broom caused, for example, by *Nectria* species, for example *Nectria galligena*;

Wilt diseases caused, for example, by *Monilinia* species, for example *Monilinia laxa*;

Leaf blister or leaf curl diseases caused, for example, by *Exobasidium* species, for example *Exobasidium vexans*;

*Taphrina* species, for example *Taphrina deformans*;

Decline diseases of wooden plants caused, for example, by Esca disease, caused for example by *Phaemoniella clamydospora, Phaeoacremonium aleophilum* and *Fomitiporia mediterranea; Eutypa* dyeback, caused for example by *Eutypa lata; Ganoderma* diseases caused for example by *Ganoderma boninense; Rigidoporus* diseases caused for example by *Rigidoporus lignosus*;

Diseases of flowers and seeds caused, for example, by *Botrytis* species, for example *Botrytis cinerea*;

Diseases of plant tubers caused, for example, by *Rhizoctonia* species, for example *Rhizoctonia solani; Helminthosporium* species, for example *Helminthosporium solani*;

Club root caused, for example, by *Plasmodiophora* species, for example *Plamodiophora brassicae*;

Diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

It is also possible to control resistant strains of the organisms mentioned above.

The triazoles can be used for curative or protective/preventive control of phytopathogenic fungi. The triazoles can be applied to the seed, the plant or plant parts, the fruit or the soil in which the plants grow.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The plants and/or plant parts can be treated one time or more than one time, such as 2 times, 3 times, 4 times, 5 times or 6 times. The time interval between two treatments can be chosen according to the agronomical needs.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Preference is given to maize, cereals, such as wheat, rye, rice, barley, oats, millet and triticale, and oil seeds. Particular preference is given to oil seeds, preferably *Brassica* oil seeds such as *Brassica napus* (e.g. canola, rapeseed). Further particular preference is given to cereals, preferably to wheat.

The present invention further relates to the above mentioned use of Prothioconazole, wherein the plant is a transgenic plant.

Genetically modified organisms are for example plants or seeds. Genetically modified plants are plants whose genome has, stably integrated, a certain heterologous gene coding for a certain protein. Here, "heterologous gene" is meant to be understood as a gene which confers novel agronomical properties on the transformed plant, or a gene which improves the agronomical quality of the modified plant.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape, and also fruit plants (with the fruits apples, pears, citrus fruits and grapes), and particular emphasis is given to maize, soya beans, potatoes, cotton, and oilseed rape. "Traits" that are emphasized are in particular increased defense of the plants against insects by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potatoes). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize) Herbicide-resistant plants (plants bred in a conventional manner for herbicide tolerance) which may be mentioned include the varieties sold under the name Clearfield® (for example maize) Of course, these statements also apply to plant cultivars having these genetic traits or genetic traits still to be developed, which plant cultivars will be developed and/or marketed in the future.

The use of Prothioconazole according to the present invention also increases the plant's resistance against abiotic stresses.

Non-limiting examples of abiotic stresses in accordance with the invention include drought, cold temperature exposure, heat exposure, osmotic stress, flooding, increased soil salinity, increased mineral exposure, ozone exposure, high light exposure, UV light exposure, limited availability of nitrogen nutrients, limited availability of phosphorus nutrients, shade avoidance.

The present invention also relates to a method of treating a plant or plant parts or seeds with Prothioconazole for indusing host defence responses in the plant.

Preferably the present invention therefore relates to a method of treating a plant or plant parts or seeds for inducing systemic acquired resistance (SAR).

More preferably the present invention therefore relates to a method of treating a plant or plant parts or seeds for inducing accumulation of salicylic acid (SA) in the plant.

More preferably the present invention therefore relates to a method of treating a plant or plant parts or seeds for inducing expression of defense genes in the plant.

The present invention also relates to a method of inducing host defence responses in a plant wherein a plant or plant parts or seeds are treated with Prothioconazole.

Preferably the present invention relates to a method of inducing systemic acquired resistance (SAR) in a plant wherein a plant or plant parts or seeds are treated with Prothioconazole.

Preferably the present invention relates to a method of inducing accumulation of salicylic acid (SA) in a plant wherein a plant or plant parts or seeds are treated with Prothioconazole.

Preferably the present invention relates to a method of inducing expression of defense genes in a plant wherein a plant or plant parts or seeds are treated with Prothioconazole.

For the use according to the present invention Prothioconazole can be used as the sole agrochemically active compound or in combination with at least one further agrochemically active compound.

The invention further relates to the above mentioned use of Prothioconazole, wherein Prothioconazole is used in combination with at least one further agrochemically active compound.

In the present context, agrochemically active compounds are to be understood as meaning all substances which are or may be customarily used for treating plants. Fungicides, bactericides, insecticides, acaricides, nematicides, molluscicides, safeners, plant growth regulators and plant nutrients as well as biological control agents may be mentioned as being preferred.

Examples of fungicides which may be mentioned are:
Group 1:
Inhibitors of the ergosterol biosynthesis, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl] 1H-imidazole-1-carbothioate, (1.65) Pyrisoxazole;
Group 2:
Inhibitors of the respiratory chain at complex I or II, for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxyl)phenyl]-3-(trifluoromethyl)-1H-pyrazole-4-carboxamide, (2.25) 3-(difluoromethyl)-1-methyl-N-[2-(1,1,2,2-tetrafluoroethoxyl)phenyl]-1H-pyrazole-4-carboxamide, (2.26) 3-(difluoromethyl)-N-[4-fluoro-2-(1,1,2,3,3,3-hexafluoropropoxyl)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) N-[1-(4-isopropoxy-2-methylphenyl)-2-methyl-1-oxopropan-2-yl]-3-methylthiophene-2-carboxamide;
Group 3:
Inhibitors of the respiratory chain at complex III, for example (3.1) ametoctradin, (3.2) amisulbrom, (3.3) azoxystrobin, (3.4) cyazofamid, (3.5) coumethoxystrobin, (3.6)

coumoxystrobin, (3.7) dimoxystrobin, (3.8) enoxastrobin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) Fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl(2E)-2-{2-[({cyclopropyl[(4-methoxyphenyl)imino]methyl}sulfanyl)methyl]phenyl}-3-methoxyacxylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide;

Group 4:
Inhibitors of the mitosis and cell division, for example (4.1) benomyl, (4.2) carbendazim, (4.3) chlorfenazole, (4.4) diethofencarb, (4.5) ethaboxam, (4.6) fluopicolide, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl) [1,2,4]triazolo[1,5-a]pyrimidine, (4.14) 3-chloro-5-(6-chloropyridin-3-yl)-6-methyl-4-(2,4,6-trifluorophenyl)pyridazine;

Group 5:
Compounds capable to have a multisite action, for example (5.1) bordeaux mixture, (5.2) captafol, (5.3) captan, (5.4) chlorothalonil, (5.5) copper hydroxide, (5.6) copper naphthenate, (5.7) copper oxide, (5.8) copper oxychloride, (5.9) copper (2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine;

Group 6:
Compounds capable to induce a host defence, for example (6.1) acibenzolar-S-methyl, (6.2) isotianil, (6.3) phosphonate, (6.4) fosetyl-aluminium, (6.5) probenazole, (6.6) saccharine, (6.7) tiadinil, (6.8) 2,6-dichloroiso nicotinic acid and its derivatives, (6.9) 3,5-dichloroanthranilic acid and its derivatives, (6.10) betaaminobutyric acid and its derivatives, (6.10) laminarin, (6.11) beta-glucans, (6.12) heptamaloxyloglucan, (6.13) rhamnolipids, (6.14) chitin or chitin fragments; (6.15) lipochitooligosaccharides, (6.16) harpin protein, (6.17) humic acids, (6.18) lignin fragments and their derivatives; preferably (6.1) acibenzolar-S-methyl, (6.2) isotianil, (6.5) probenazole, (6.7) tiadinil, (6.10) laminarin;

Group 7:
Inhibitors of the amino acid and/or protein biosynthesis, for example (7.1) andoprim, (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline, (7.9) oxytetracycline, (7.10) streptomycin;

Group 8:
Inhibitors of the ATP production, for example (8.1) fentin acetate, (8.2) fentin chloride, (8.3) fentin hydroxide, (8.4) silthiofam;

Group 9:
Inhibitors of the cell wall synthesis, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate, (9.10) polyoxin B;

Group 10:
Inhibitors of the lipid and membrane synthesis, for example (10.1) biphenyl, (10.2) chloroneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene, (10.15) tolclofos-methyl;

Group 11:
Inhibitors of the melanin biosynthesis, for example (11.1) carpropamid, (11.2) diclocymet, (11.3) fenoxanil, (11.4) phthalide, (11.5) pyroquilon, (11.6) tricyclazole, (11.7) 2,2,2-trifluoroethyl {3-methyl-1-[(4-methylbenzoy)amino]butan-2-yl}carbamate;

Group 12:
Inhibitors of the nucleic acid synthesis, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazol, (12.9) metalaxyl, (12.10) metalaxyl-M (mefenoxam), (12.11) ofurace, (12.12) oxadixyl, (12.13) oxolinic acid, (12.14) octhilinone;

Group 13:
Inhibitors of the signal transduction, for example (13.1) chlozolinate, (13.2) fenpiclonil, (13.3) fludioxonil, (13.4) iprodione, (13.5) procymidone, (13.6) quinoxyfen, (13.7) vinclozolin, (13.8) proquinazid;

Group 14:
Compounds capable to act as an uncoupler, for example (14.1) binapacryl, (14.2) dinocap, (14.3) ferimzone, (14.4) fluazinam, (14.5) meptyldinocap;

Group 15:
Further compounds, for example (15.1) benthiazole, (15.2) bethoxazin, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat metilsulfate, (15.17) diphenylamine, (15.18) ecomate, (15.19) fenpyrazamine, (15.20) flumetover, (15.21) fluoroimide, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.37) oxamocarb, (15.38) oxyfenthiin, (15.39) pentachlorophenol and salts, (15.40) phenothrin, (15.41) phosphorous acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2- chloropyridin-4-yl)-1-(morpholin-4-yl)prop-2-en-1-one, (15.47) pyrrolnitrine, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutpyloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulfonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide, (15.74) 5-fluoro-2-[(4-fluorobenzyl)oxy]pyrimidin-4-amine, (15.75) 5-fluoro-2-[(4-methylbenzyl)oxy]pyrimidin-4-amine, (15.76) 5-methyl-6-octyl[1,2,4]triazolo[1,5-a]pyrimidin-7-amine, (15.77) ethyl(2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulfate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulfonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (mesomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2- chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulfanyl)-1-{[rel(2R,3S)-3-(2-chlorophenyl)-2-(2,4-difluorophenyl)oxiran-2-yl]methyl}-1H-1,2,4-triazole, (15.136) 5-(allylsulfanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) Abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazole-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide.

Preferably Prothioconazole is used in combination with at least one of the following fungicides:
tebuconazole, epoxiconazole, metconazole, cyproconazole, propiconazole, flusilazole, difenoconazole, prochloraz, triadimenol, pencycuron, fluopyram, bixafen, N-(5-chloro-2-isopropylbenzyl)-N-cyclopropyl-3-(difluoromethyl)-5-fluoro-1-methyl-1H-pyrazole-4-carboxamide, boscalid, isopyrazam, benzovindiflupyr, penthiopyrad, fluxapyroxad, spiroxamine, metrafenone, pyriofenone, fenpropidin, fenpropimorph, proquinazid, cyflufenamid, cyprodinil, chlorothalonil, 2,6-Dimethyl-1H,5H-[1,4]dithiino[2,3-c:5,6-c']dipyrrole-1,3,5,7(2H,6H)-tetrone, trifloxystrobin, fluoxastrobin, azoxystrobin, picoxystrobin, pyraclostrobin, dimoxystrobin, kresoxim-methyl, paclobutrazol.

Examples of bactericides which may be mentioned are: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Examples of insecticides, acaricides and nematicides which may be mentioned are:

(1) Acetylcholinesterase (AChE) inhibitors, for example carbamates, e.g. alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, and xylylcarb; or organophosphates, e.g. acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl, O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, and imicyafos.

(2) GABA-gated chloride channel antagonists, for example organochlorines, e.g. camphechlor, chlordane, endosulfan, gamma-HCH, HCH, heptachlor, lindane, and methoxychlor; or fiproles (phenylpyrazoles), e.g. acetoprole, ethiprole, fipronil, pyrafluprole, pyriprole, and vaniliprole.

(3) Sodium channel modulators/voltage-dependent sodium channel blockers, for example pyrethroids, e.g. acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrin (pyrethrum), eflusilanat; DDT; or methoxychlor.

(4) Nicotinergic acetylcholine receptor agonists/antagonists, for example chloronicotinyls, e.g. acetamiprid, clothianidin, dinotefuran, imidacloprid, imidaclothiz, nitenpyram, nithiazine, thiacloprid, thiamethoxam, AKD-1022; or nicotine, bensultap, cartap, thiosultap-sodium, and thiocylam.

(5) Allosteric acetylcholine receptor modulators (agonists), for example spinosyns, e.g. spinosad and spinetoram.

(6) Chloride channel activators, for example mectins/macrolides, e.g. abamectin, emamectin, emamectin benzoate, ivermectin, lepimectin, and milbemectin; or juvenile hormone analogues, e.g. hydroprene, kinoprene, methoprene, epofenonane, triprene, fenoxycarb, pyriproxifen, and diofenolan.

(7) Active ingredients with unknown or non-specific mechanisms of action, for example gassing agents, e.g. methyl bromide, chloropicrin and sulfuryl fluoride; selective antifeedants, e.g. cryolite, pymetrozine, pyrifluquinazon and flonicamid; or mite growth inhibitors, e.g. clofentezine, hexythiazox, etoxazole.

(8) Oxidative phosphorylation inhibitors, ATP disruptors, for example diafenthiuron; organotin compounds, e.g. azocyclotin, cyhexatin and fenbutatin oxide; or propargite, tetradifon.

(9) Oxidative phoshorylation decouplers acting by interrupting the H proton gradient, for example chlorfenapyr, binapacryl, dinobuton, dinocap and DNOC.

(10) Microbial disruptors of the insect gut membrane, for example *Bacillus thuringiensis* strains.

(11) Chitin biosynthesis inhibitors, for example benzoylureas, e.g. bistrifluron, chlorfluazuron, diflubenzuron, fluazuron, flucycloxuron, flufenoxuron, hexaflumuron, lufenuron, novaluron, noviflumuron, penfluron, teflubenzuron or triflumuron.

(12) Buprofezin.

(13) Moulting disruptors, for example cyromazine

(14) Ecdysone agonists/disruptors, for example diacylhydrazines, e.g. chromafenozide, halofenozide, methoxyfenozide, tebufenozide, and Fufenozide (JS118); or azadirachtin.

(15) Octopaminergic agonists, for example amitraz.

(16) Site III electron transport inhibitors/site II electron transport inhibitors, for example hydramethylnon; acequinocyl; fluacrypyrim; or cyflumetofen and cyenopyrafen.

(17) Electron transport inhibitors, for example Site I electron transport inhibitors, from the group of the METI acaricides, e.g. fenazaquin, fenpyroximate, pyrimidifen, pyridaben, tebufenpyrad, tolfenpyrad, and rotenone; or voltage-dependent sodium channel blockers, e.g. indoxacarb and metaflumizone.

(18) Fatty acid biosynthesis inhibitors, for example tetronic acid derivatives, e.g. spirodiclofen and spiromesifen; or tetramic acid derivatives, e.g. spirotetramat.

(19) Neuronal inhibitors with unknown mechanism of action, e.g. bifenazate.

(20) Ryanodine receptor effectors, for example diamides, e.g. flubendiamide, (R),(S)-3-chloro-N$^1$-{2-methyl-4-[1,2,2,2-tetrafluoro-1-(trifluoromethyl)ethyl]phenyl}-N$^2$-(1-methyl-2-methylsulphonyl-ethyl)phthalamide, chlorantraniliprole (Rynaxypyr), or Cyantraniliprole (Cyazypyr).

(21) Further active ingredients with unknown mechanism of action, for example amidoflumet, benclothiaz, benzoximate, bromopropylate, buprofezin, chinomethionat, chlordimeform, chlorobenzilate, clothiazoben, cycloprene, dicofol, dicyclanil, fenoxacrim, fentrifanil, flubenzimine, flufenerim, flutenzin, gossyplure, japonilure, metoxadiazone, petroleum, potassium oleate, pyridalyl, sulfluramid, tetrasul, triarathene or verbutine; or one of the following known active compounds 4-{[(6-bromopyrid-3-yl)methyl](2-fluoroethyl)-amino}furan-2(5H)-one, 4-{[(6-fluoropyrid-3-yl)methyl](2,2-difluoroethyl)amino}furan-2(5H)-one, 4-{[(2-chloro-1,3-thiazol-5-yl)methyl](2-fluoroethyl)amino}furan-2(5H)-one, 4-{[(6-chloropyrid-3-yl)methyl](2-fluoroethyl)amino}furan-2(5H)-one, 4-{[(6-chloropyrid-3-yl)methyl](2,2-difluoroethyl)amino}furan-2(5H)-one (all known from WO 2007/115644), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl]

(methyl)amino}furan-2(5H)-one, 4-{[(6-chloro-5-fluoropyrid-3-yl)methyl](cyclopropyl)amino}furan-2(5H)-one (both from WO 2007/115643), 4-{[(6-chloropyrid-3-yl)methyl](cyclopropyl)amino}furan-2(5H)-one, 4-{[(6-chloropyrid-3-yl)methyl](methyl)amino}furan-2(5H)-one (both from EP-A-0 539 588), [(6-chloropyridin-3-yl)methyl](methyl)oxido-$\lambda^4$-sulfanylidene cyanamide, [1-(6-chloropyridin-3-yl)ethyl](methyl)oxido-$\lambda^4$-sulfanylidene cyanamide (both from WO 2007/149134) and its diastereomeres (A) and (B)

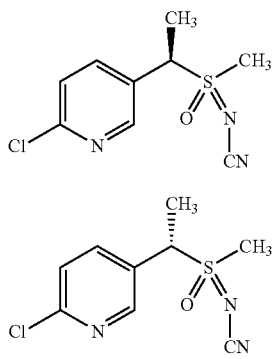

(also known from WO 2007/149134), [(6-trifluoromethylpyridin-3-yl)methyl](methyl)oxido-$\lambda^4$-sulfanylidene cyanamide (known from WO 2007/095229), or [1-(6-trifluoromethylpyridin-3-yl)ethyl](methyl)-oxido-$\lambda^4$-sulfanylidene cyanamide (known from WO 2007/149134) and its diastereomeres (C) and (D), namely Sulfoxaflor (also known from WO 2007/149134)

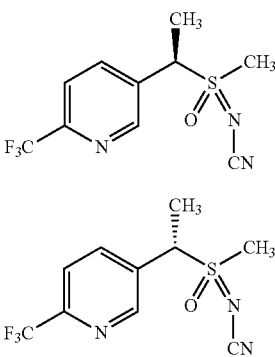

Examples of molluscicides which may be mentioned are metaldehyde and methiocarb.

Examples of safeners which may be mentioned are:
(1) Heterocyclic carboxylic acid derivates, for example dichlorophenylpyrazolin-3-carboxylic acid derivatives, e.g. 1-(2,4-dichlorophenyl)-5-(ethoxycarbonyl)-5-methyl-4,5-dihydro-1H-pyrazole-3-carboxylic acid, diethyl 1-(2,4-dichlorophenyl)-4,5-dihydro-5-methyl-1H-pyrazole-3,5-dicarboxylate ("mefenpyr-diethyl"), and similar compounds known from WO 91/07874; for example dichlorophenylpyrazolecarboxylic acid derivatives, e.g. ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 5-tert-butyl-1-(2,4-dichlorophenyl)-1H-pyrazole-3-carboxylate and similar compounds known from EP-A 0 333 131 and EP-A 0 269 806; for example 1,5-diphenylpyrazole-3-carboxylic acid derivatives, e.g. ethyl 1-(2,4-dichlorophenyl)-5-phenyl-1H-pyrazole-3-carboxylate, methyl 1-(2-chlorophenyl)-5-phenyl-1H-pyrazole-3-carboxylate, and similar compounds known from EP-A 0 268 554; for example triazolecarboxylic acid derivatives, e.g. fenchlorazole, fenchlorazole-ethyl, and similar compounds known from EP-A 0 174 562 and EP-A 0 346 620; for example 2-isoxazoline-3-carboxylic acid derivatives, e.g. ethyl 5-(2,4-dichlorobenzyl)-4,5-dihydro-1,2-oxazole-3-carboxylate, ethyl 5-phenyl-4,5-dihydro-1,2-oxazole-3-carboxylate and similar compounds known from WO 91/08202, or 5,5-diphenyl-4,5-dihydro-1,2-oxazole-3-carboxylic acid, ethyl 5,5-diphenyl-4,5-dihydro-1,2-oxazole-3-carboxylate ("isoxadifen-ethyl"), propyl 5,5-diphenyl-4,5-dihydro-1,2-oxazole-3-carboxylate, ethyl 5-(4-fluorophenyl)-5-phenyl-4,5-dihydro-1,2-oxazole-3-carboxylate known from WO 95/07897.

(2) Derivatives of 8-quinolinol, for example derivatives of (quinolin-8-yloxy)acetic acid, e.g. heptan-2-yl[(5-chloroquinolin-8-yl)oxy]acetate ("cloquintocet-mexyl"), 4-methylpentan-2-yl[(5-chloroquinolin-8-yl)oxy]acetate, 4-(allyloxy)butyl[(5-chloroquinolin-8-yl)oxy]acetate, 1-(allyloxy)propan-2-yl[(5-chloroquinolin-8-yl)oxy]acetate, ethyl[(5-chloroquinolin-8-yl)oxy]acetate, methyl[(5-chloroquinolin-8-yl)oxy]acetate, allyl[(5-chloroquinolin-8-yl)oxy]acetate, 2-{[propylideneamino]oxy}ethyl[(5-chloroquinolin-8-yl)oxy]acetate, 2-oxopropyl[(5-chloroquinolin-8-yl)oxy]acetate, and similar compounds to known from EP-A 0 086 750, EP-A 0 094 349, EP-A 0 191 736 or EP-A 0 492 366, as well as [(5-chloroquinolin-8-yl)oxy]acetic acid, its hydrates and salts, e.g. the lithium, sodium, potassium, calcium, magnesium, aluminum, iron, ammonium, quartanary ammonium, sulfonium or phosphonium salts as known from WO 02/34048; for example derivatives of [(5-chloroquinolin-8-yl)oxy]malonic acid, e.g diethyl[(5-chloroquinolin-8-yl)oxy]malonate, diallyl[(5-chloroquinolin-8-yl)oxy]malonate, ethyl methyl[(5-chloroquinolin-8-yl)oxy]malonate, and similar compounds known from EP-A 0 582198.

(3) Dichloroacetamides, which are often used as pre-emergence safeners (soil active safeners), e.g. "dichlormid" (N,N-diallyl-2,2-dichloroacetamide), "R-29148" (3dichloroacetyl-2,2,5-trimethyl-1,3-oxazolidine) and "R-28725" (3-dichloroacetyl-2,2,-dimethyl-1,3-oxazolidine) both of the company Stauffer, "benoxacor" (4-dichloroacetyl-3,4-dihydro-3-methyl-2H-1,4-benzoxazine), "PPG-1292" (N-allyl-N-[(1,3-dioxolan-2-yl)methyl]-dichloroacetamide) of PPG Industries, "DKA-24" (N-allyl-N-[(allylaminocarbonyl)methyl]-dichloroacetamide) of Sagro-Chem, "AD-67" or "MON 4660" (3-dichloroacetyl-1-oxa-3-aza-spiro[4,5]decane) of Nitrokemia and Monsanto, "TI-35" (1-dichloroacetyl-azepane) of TRI-Chemical RT, "diclonon" (dicyclonon) or "BAS145138" or "LAB145138" (3-dichloroacetyl-2,5,5-trimethyl-1,3-diazabicyclo[4.3.0]nonane) of BASF, "Furilazol" or "MON 13900" [(RS)-3-dichloroacetyl-5-(2-furyl)-2,2-dimethyloxazolidine], as well as there (R)-isomer.

(4) Acylsulfonamides, for example N-acylsulfonamide of the formula (II)

(II)

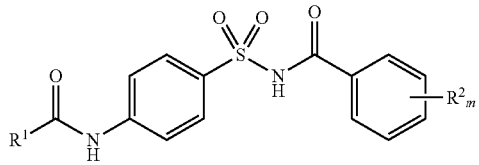

or its salts (known from WO 97/45016), wherein
$R^1$ represents $(C_1-C_6)$alkyl, which is unsubstituted or mono- to trisubstituted by substituents selected from the group consisting of halogen, $(C_1-C_4)$alkoxy, $(C_1-C_6)$haloalkoxy and $(C_1-C_4)$alkylthio;
$R^2$ represents halogen, $(C_1-C_4)$alkyl, $(C_1-C_4)$alkoxy, $CF_3$;
m is 1 or 2;
or for example 4-(benzoylsulfamoyl)benzamides of the formula (III)

(III)

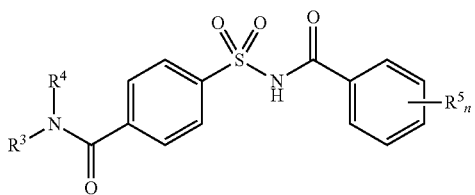

or its salts (known from WO 99/16744), wherein
$R^3$, $R^4$ independently of one another represent hydrogen, $(C_1-C_6)$alkyl, $(C_3-C_6)$alkenyl, $(C_3-C_6)$alkynyl, $(C_3-C_6)$cycloalkyl,
$R^5$ represents halogen, $(C_1-C_4)$alkyl, $(C_1-C_4)$haloalkyl or $(C_1-C_4)$alkoxy
n is 1 or 2,
in particular compounds of formula (III), wherein
$R^3$=cyclopropyl, $R^4$=hydrogen and $R^5_n$=2-OMe, ("cyprosulfamide"),
$R^3$=cyclopropyl, $R^4$=hydrogen and $R^5_n$=5-Cl-2-OMe,
$R^3$=ethyl, $R^4$=hydrogen and $R^5_n$=2-OMe,
$R^3$=isopropyl, $R^4$=hydrogen and $R^5_n$=5-Cl-2-OMe,
$R^3$=isopropyl, $R^4$=hydrogen and $R^5_n$=2-OMe.
or for example benzoylsulfamoylphenylureas of the formula (IV)

(IV)

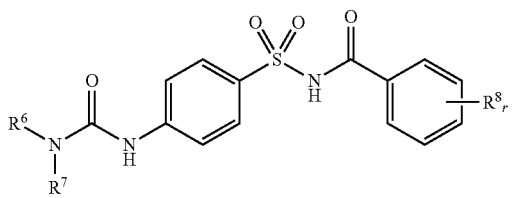

(known from EP-A 0 365 484), wherein
$R^6$, $R^7$ independently of one another represent hydrogen, $(C_1-C_8)$alkyl, $(C_3-C_6)$alkenyl, $(C_3-C_6)$alkynyl,
$R^8$ represents halogen, $(C_1-C_4)$alkyl, $(C_1-C_4)$alkoxy, $CF_3$
r is 1 or 2;
in particular
1-[4-(N-2-methoxybenzoylsulfamoyl)phenyl]-3-methyl urea,
1-[4-(N-2-methoxybenzoylsulfamoyl)phenyl]-3,3-dimethyl urea,
1-[4-(N-4,5-dimethylbenzoylsulfamoyl)phenyl]-3-methyl urea.

(5) Hydroxyaromatic compounds and aromatic-aliphatic carboxylic acid derivatives, e.g. ethyl 3,4,5-triacetoxybenzoate, 4-hydroxy-3,5-dimethoxybenzoic acid, 3,5-dihydroxybenzoic acid, 2,4-dihydroxybenzoic acid, 4-fluoro-2-hydroxybenzoic acid, 2-hydroxycinnamic acid, 2,4-dichlorocinnamic acid (cf. WO 2004/084631, WO 2005/015994, WO 2005/016001).

(6) 1,2-Dihydrochinoxalin-2-ones, e.g. 1-methyl-3-(2-thienyl)-1,2-dihydrochinoxalin-2-one, 1-methyl-3-(2-thienyl)-1,2-dihydrochinoxalin-2-thione, 1-(2-aminoethyl)-3-(2-thienyl)-1,2-dihydrochinoxalin-2-one hydrochlorid, 1-(2-methylsulfonylaminoethyl)-3-(2-thienyl)-1,2-dihydrochinoxalin-2-one (cf. WO 2005/112630).

(7) Diphenylmethoxyacetic acid derivatives, e.g. methyl (diphenylmethoxy)acetate (CAS-Reg. No. 41858-19-9), ethyl (diphenylmethoxy)acetate or (diphenylmethoxy)acetic acid (cf. WO 98/38856).

(8) Compounds of formula (V)

(V)

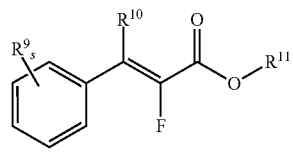

or its salts (known from WO 98/27049), wherein
$R^9$ represents halogen, $(C_1-C_4)$alkyl, $(C_1-C_4)$haloalkyl, $(C_1-C_4)$alkoxy, $(C_1-C_4)$haloalkoxy,
$R^{10}$ represents hydrogen or $(C_1-C_4)$alkyl,
$R^{10}$ represents hydrogen, in each case unsubstituted or mono- to trisubstituted $(C_1-C_8)$alkyl, $(C_2-C_4)$alkenyl, $(C_2-C_4)$alkynyl, or aryl, where the substituents are selected from the group consisting of halogen and $(C_1-C_8)$alkoxy,
s is 0, 1 or 2.

(9) 3-(5-Tetrazolylcarbonyl)-2-chinolones, e.g. 1,2-dihydro-4-hydroxy-1-ethyl-3-(5-tetrazolylcarbonyl)-2-chinolone (CAS-Reg. No. 219479-18-2), 1,2-dihydro-4-hydroxy-1-methyl-3-(5-tetrazolyl-carbonyl)-2-chinolone (CAS-Reg. No. 95855-00-8) (cf. WO 99/00020).

(10) Compounds of the formulae (VI-a) and (VI-b)

(V)

(VI-a)

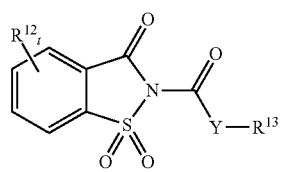

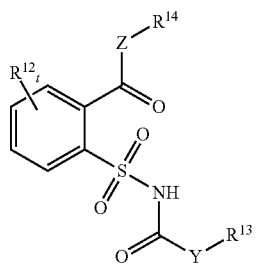

(VI-b)

(known from WO 2007/023719 and WO 2007/023764), wherein $R^{12}$ represents halogen, $(C_1-C_4)$alkyl, methoxy, nitro, cyano, $CF_3$, $OCF_3$, Y, Z independently represent O or S, t is 0, 1, 2, 3 or 4, $R^{13}$ represents $(C_1-C_{16})$alkyl, $(C_2-C_6)$alkenyl, aryl, benzyl, halogenobenzyl, $R^{14}$ represents hydrogen or $(C_1-C_6)$alkyl.

(11) Oxyimino compounds, known as seed treatment agents, e.g. "oxabetrinil" [(Z)-1,3-dioxolan-2-ylmethoxyimino(phenyl)acetonitril], "fluxofenim" [1-(4-chlorophenyl)-2,2,2-trifluoro-1-ethanone-O-(1,3-dioxolan-2-ylmethyl)-oxime], and "cyometrinil" or "CGA-43089" [(Z)-cyanomethoxy-imino(phenyl)acetonitril], all known as seed treatment safener for sorghum against damage by metolachlor.

(12) Isothiochromanones, e.g. methyl[(3-oxo-1H-2-benzothiopyran-4(3H)-ylidene)methoxy]acetate (CAS-Reg. No. 205121-04-6) and similar compounds known from WO 98/13361.

(13) Compounds from the group consisting of "naphthalic anhydrid" (1,8-naphthalinedicarboxylic acid anhydride), which is known as seed treatment safener for corn (maize) against damage by thiocarbamate herbicides, "fenclorim" (4,6-dichloro-2-phenylpyrimidine), which is known as seed treatment safener in sown rice against damage by pretilachlor, "flurazole" (benzyl-2-chloro-4-trifluoromethyl-1,3-thiazol-5-carboxylate), which is known as seed treatment safener for sorghum against damage by alachlor and metolachlor, "CL 304415" (CAS-Reg. No. 31541-57-8), (4-carboxy-3,4-dihydro-2H-1-benzopyran-4-acetic acid) of American Cyanamid, which is known as safener for corn (maize) against damage by imidazolinones, "MG 191" (CAS-Reg. No. 96420-72-3) (2-dichloromethyl-2-methyl-1,3-dioxolane) of Nitrokemia, known as safener for corn (maize), "MG-838" (CAS-Reg. No. 133993-74-5), (2-propenyl 1-oxa-4-azaspiro[4.5]decane-4-carbodithioate) of Nitrokemia, "Disulfoton" (O,O-diethyl-S-2-ethylthioethyl phosphorodithioate), "dietholate" (O,O-diethyl-O-phenyl-phosphorothioate), "mephenate" (4-chlorophenyl-methyl-carbamate).

(14) Compounds, which besides herbicidal activity als exhibit Safener activity in crops like rice, e.g. "Dimepiperate" or "MY-93" (S-1-methyl-1-phenylethyl-piperidin-1-carbothioate), which is known as safener for rice against damage by molinate, "daimuron" or "SK 23" [1-(1-methyl-1-phenylethyl)-3-p-tolyl-urea], which is known as safener for rice against damage by imazosulfuron, "cumyluron"="JC-940" [3-(2-chlorophenylmethyl)-1-(1-methyl-1-phenyl-ethyl)urea] (cf. JP-A 60-087254), which is known as safener for rice against damage by some herbicides, "methoxyphenon" or "NK 049" (3,3'-dimethyl-4-methoxybenzophenone), which is known as safener for rice against damage by some herbicides, "CSB" [1-bromo-4-(chloromethylsulfonyflbenzene] of Kumiai (CAS-Reg. No. 54091-06-4), which is known as safener for rice against damage by some herbicides.

(15) Compounds, which are mainly used as herbicides, but which exhibit also safener activity on some crops, e.g. (2,4-dichlorophenoxy)acetic acid (2,4-D), (4-chlorophenoxy)acetic acid, (R,S)-2-(4-chlor-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyBethyl-3,6-dichloro-2-methoxybenzoate (lactidichlor-ethyl).

Particularly preferred examples of safeners are dichlorophenylpyrazolin-3-carboxylic acid derivatives, e.g. 1-(2,4-dichlorophenyl)-5-(ethoxycarbonyl)-5-methyl-4,5-dihydro-1H-pyrazole-3-carboxylic acid, diethyl 1-(2,4-dichlorophenyl)-4,5-dihydro-5-methyl-1H-pyrazole-3,5-dicarboxylate ("mefenpyr-diethyl"), and similar compounds known from WO 91/07874. Most preferred examples of safeners is mefenpyr-diethyl. Examples of plant growth regulators which may be mentioned are chlormequat chlorure, chlorocholine chloride and ethephon.

Examples of plant nutrients which may be mentioned are customary inorganic or organic fertilizers for supplying plants with macro- and/or micronutrients.

Examples of biological control agents which may be mentioned are yeasts and bacteria, e.g. Metschnikowia fructicola or *bacillus firmus*.

Preferred fungicidal or insecticidal active compounds are selected from the group consisting of *bacillus firmus*, beta-cyfluthrin, bixafen, clothianidin, ethiprole, fenamidone, fenhexamid, fipronil, flubendiamide, fluopicolide, fluopyram, fluoxastrobin, fosetyl-Al, imidacloprid, iprovalicarb, isotianil, methiocarb, metominostrobin, oryzastrobin, pencycuron, penflufen, prochloraz-manganese chloride, propamocarb, propineb, pyrimethanil, rynaxypyr, sedaxane, spinosad, spiroxamine, thiacloprid, tiadinil, thiamethoxam, thifluzamide, thiodicarb, trifloxystrobin, and 4-{[(6-chloropyrid-3-yl)methyl](2,2-difluoroethyl)amino}furan-2(5H)-one.

The Prothioconazole used according to the present invention is generally applied in form of a composition comprising at least Prothioconazole as mentioned above. Preferably the fungicidal composition comprises agriculturally acceptable additives, solvents, carriers, surfactants, or extenders.

The present invention furthermore relates to compositions comprising Prothioconazole or combinations of Prothioconazole with optionally at least one further agrochemically active compound. Preferably, the compositions are fungicidal compositions comprising agriculturally suitable carriers or extenders.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are: for example lignosulphite waste liquors and methylcellulose.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions used according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions used according to the invention comprise between 0.05 and 99 percent by weight, 0.01 and 98 percent by weight, preferable between 0.1 and 95 percent by weight, particularly preferred between 0.5 and 90 percent by weight of the active compound or active compound combinations used according to the invention, very particularly preferable between 10 and 70 percent by weight.

The active compound compositions or combinations used according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The formulations generally comprise between 0.1 and 95% by weight of active compound(s), preferably between 0.5 and 90%.

The active compound combinations according to the invention can be present in (commercial) formulations and in the use forms prepared from these formulations as a mixture with other active compounds, such as insecticides, attractants, sterilants, bactericides, acaricides, nematicides, fungicides, growth regulators or herbicides. A mixture with fertilizers is also possible.

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. Preference is given to application by dipping, spraying, atomizing, irrigating, evaporating, dusting, fogging, broadcasting, foaming, painting, spreading-on, watering (drenching) and drip irrigating.

The application of the formulations is carried out in accordance with customary agricultural practice in a manner adapted to the application forms. Customary applications are, for example, dilution with water and spraying of the resulting spray liquor, application after dilution with oil, direct application without dilution, seed dressing or soil application of carrier granules.

The compositions according to the invention do not only comprise ready-to-use compositions which can be applied with suitable apparatus to the plant or the seed, but also commercial concentrates which have to be diluted with water prior to use.

According to the present invention the application rates can be varied within a relatively wide range, depending on the kind of application. The application rate of the active ingredients is in the case of treatment of plants or plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 50 g per 100 kg of seed, even more preferably from 2.5 to 30 g per 100 kg of seed.

These application rates are merely by way of example and are not limiting for the purposes of the invention.

In the case of treatment of seeds at least an application rate of 2.5 g per 100 kg of seed is preferred, in particular to induce systemic acquired resistance (SAR).

In the case of treatment of plants or plant parts at least an application rate of 50 g/ha is preferred, in particular to induce systemic acquired resistance (SAR).

The invention is illustrated by—but not limited to—the examples below.

Examples

1. Induction of Salicylic Acid Accumulation in Oilseed Rape

Rape plants were raised in pots in the glass house. Four week old plants were sprayed with the fungicide compositions. Before spraying, on the next day, on the third day and on the 7$^{th}$ day after spraying single leaves were cut off and stored frozen in liquid nitrogen for salicylic acid analysis. Frozen leaves were powdered and extracted in a mixture of 2-propanol/water/concentrated HCl (2:1:0.002) and finally salicylic acid levels were directly determined by HPLC-MS as described by Xiangqing Pan et al. (in: *Nature Protocols* (2010), 5(6), 986-992).

Salicylic acid level in untreated leaves before fungicide composition spraying was ~70 nMol/kg freshweight. As shown in Table 1 treatment with fungicide compositions comprising Prothiocionazole led to a dramatic increase of salicylic acid in the leaves on the first day after treatment. The fungicide composition Proline® eg. increased the salicylic acid level to 2,594 nMol/kg freshweight. On the third day the salicylic acid levels were still significantly increased, while after 7 days salicylic acid levels returned back close to untreated controls. In comparative experiments with the non-azole fungicide Propineb (fungicide composition Antracol®) as well as a the triazole fungicide Tebuconazole (fungicide composition Folicur®), no substantial influence on the salicylic acid level in sprayed rape leaves was observed. Therefore, surprisingly the effect of salicylic acid induction is specific for the fungicide Prothioconazole.

The following fungicide compositions have been used:
A: Tilmor® 1,0; Prothioconazole+Tebuconazole (applied amount corresponding to 80 g/ha+160 g/ha)
B: Tilmor® 1,2; Prothioconazole+Tebuconazole (applied amount corresponding to 96 g/ha+192 g/ha)
C: Proline®: Prothioconazole (applied amount corresponding to 125 g/ha)
D: Prosaro®; Prothioconazole+Tebuconazole (applied amount corresponding to 125 g/ha+125 g/ha)
E: Folicur®; Tebuconazole (applied amount corresponding to 68 g/ha)
F: Propulse®; Prothioconazole+Fluopyram (applied amount corresponding to 125 g/ha+125 g/ha)
G: Antracol®; Propineb (applied amount corresponding to 70 g/ha)

TABLE 1

Concentration of salicylic acid in rape leaves in nMol/kg fresh weigth. The levels of salicylic acid (SA) in 4 week old rape leaves before (0) and 1, 3 and 7 days after spraying with the respective fungicide composition are shown.

| days | A | B | C | D | E | F | G |
|---|---|---|---|---|---|---|---|
| 0 | 60 | 60 | 77 | 77 | 68 | 77 | 77 |
| 1 | 1208 | 2565 | 2594 | 2016 | 146 | 1903 | 38 |
| 3 | 235 | 397 | 374 | 293 | 67 | 430 | 39 |
| 7 | 90 | 53 | 84 | 84 | 21 | 175 | 13 |

2. Induction of Salicylic Acid Accumulation in Seed Treated Wheat Seedlings

Wheat seeds were treated with the fungicide compositions. After one hour the seeds were placed on wet filter paper and let germinating in a humid chamber. On the 7$^{th}$ day the first leaves were 4 cm long and cut off and stored frozen in liquid nitrogen for salicylic acid analysis. Frozen leaves were powdered and extracted in a mixture of 2-propanol/water/concentrated HCl (2:1:0.002) and finally salicylic acid levels were directly determined by HPLC-MS as described by Xiangqing Pan et al. (in: *Nature Protocols* (2010), 5(6), 986-992).

Salicylic acid level in leaves of untreated plants was 89±3 nMol/kg freshweight. Seed treatment with the fungicide composition Redigo® comprising Prothiocionazole (applied amount corresponding to 10 g a.i./100 kg seeds) led to a statistically highly significant increase of salicylic acid in the leaves on the seventh day after treatment to a salicylic acid level to 101±1 nMol/kg freshweight.

As to be expected the relative increase in salicylic acid level in wheat leaves seven days after seed treatment was lower than in leaf spray treated oilseed rape one day after leaf spray. As shown in Example 1, the raise in salicylic acid level was only transient, with its extreme maximum on the first day after treatment with Prothiocoazole containing fungicide compositions. After seed treatment, the occurrence of the first leave has to be awaited, therefore a measurement after one day is impossible and after seven days only a smaller raise in salicylic acid can be expected. Nevertheless the raise in wheat leaves of salicylic acid after 7 days was statistically highly significant.

3. Induction of Salicyclic Acid and Pathogen Response Pathways in *Arabidopsis thaliana*

*Arabidopsis thaliana* plants were grown on soil in climate controlled growth chambers for 33 days under defined conditions. For treatment Prothioconazole was formulated to result in a final concentration corresponding to 500 g/ha in a spray application. The plants were sprayed in biological replicates. A control group of similar grown plants was equally treated with a blank formulation. Aerial tissues of the treated plants were harvested 3 h and 6 h after treatment, frozen in liquid nitrogen and stored at −80° C. for further processing. Each biological replicate (3 per treatment and time point) consisted of a pool of 10 plants.

Total RNA was prepared from each sample using the RNeasy Midi kit from Qiagen #75142 according to the manufacturer's recommendations. The RNA was then transcribed into cDNA using Superscript II Reverse Transcriptase (Invitrogen). The biotin-labeled cRNA probes for hybridization were generated from the cDNA using the BioArray HighYield® RNA transcript labeling kit (T7) (Enzo Life Sceinces # ENZ42655-40) according the manufacturer's recommendations. The labelled cRNA probes were subsequently hybridized onto Affymetrix GeneChip *Arabidopsis* ATH1 Genome Arrays (cat.#900385).

The samples were analyzed using the Affymetrix GeneChip System. The resulting data were processed and analyzed using Genedata Refiner Array, Genedata Analyst, RobiNA (Lohse et al. 2012, Nucleic Acids Res) and MapMan (Usadel et al. 2009, Plant Cell Environment) software packages.

The analyses revealed a total number of 380 differentially expressed genes (238 up-regulated and 142 down-regulated, >2-fold change, p≤0.05) 3 h after treatment and 447 differentially expressed genes (299 up-regulated and 148 down-regulated, >2-fold change, p≤0.05) 6 h after treatment, compared to the respective controls.

In depth analyses of the obtained data indicated among others the significant up-regulation of two genes coding for UDP-glucose: salicylic acid glucosyltransferases, which are known to be upregulated by salicylic acid (SA) (At1g05680 3-fold induction after 3 h; 5.5-fold induction after 6 h and At2g43820-2.5-fold induction after 3 h and 6 h). These data speak for an increase of SA levels in Prothioconazoletreated plants. 6 h after treatment an up-regulation of typical plant defense genes was observed, e.g. At1g57630 [Toll-Interleukin-Resistance domain-containing protein]—3.4-fold induction, At1g66090 [TIR-NBS class of disease resistance protein]—2.4-fold induction, At3g59930 [Defensin-like protein 206]—3-fold induction and At4g36010 [pathogenesis-related thaumatin family protein]—3.8-fold induction. These data indicate an activation of defense-related responses in *Arabidopsis thaliana* after treatment with Prothioconazole.

4. Induction of Defense Gene Expression in *Arabidopsis thaliana*

*Arabidopsis thaliana* reporter plants containing the coding sequence of a green fluorescent protein (GFP) linked to the salicylate responsive promoter sequence of the PR1 (pathogenesis-related protein 1) gene (AT2G14610) were grown for five days and then sprayed with compounds. On the $3^{rd}$ day after spraying, plant fluorescence was assessed with a MacroFluo instrument from Leica Microsystems (Wetzlar, Germany). Fluorescences were quantified with the MetaMorph Microscopy Automation & Image Analysis Software (Molecular Devices, Sunnyvale, Calif., United States).

Background fluorescence in mock treated leaves was set as 1.00. Salicylic acid treatment (300 ppm) resulted in a relative fluorescence value of 1.96 (Table 2), proving the validity of the test system. Treatment with Prothioconazole (300 ppm) led to a relative fluorescence value of 2.04, proving resistance gene expression induction by Prothioconazole in the same magnitude as with salicylic acid. The triazol fungicide Tebuconazole, however, resulted in a relative fluorescence value of 0.73, showing not the same effect.

TABLE 2

Relative fluorescence of GFP in *Arabidopsis thaliana* expressing GFP behind the PR1 promoter; 3 days after spraying with compounds.

| Compound | Relative fluorescence | Confidence interval |
|---|---|---|
| Mock (background) | 1.00 | 0.19 |
| Salicylic acid (300 ppm) | 1.96 | 0.35 |
| Prothioconazole (300 ppm) | 2.04 | 0.46 |
| Tebuconazole (300 ppm) | 0.73 | 0.37 |

The invention claimed is:

1. A method of inducing a host defense response in a wheat or oilseed rape plant leaves comprising treating a wheat seed or oilseed rape seed with Prothioconazole in an amount and manner such that accumulation of salicylic acid (SA) in the plant grown from the seed is induced, wherein the amount is 2.5 to 30 g Prothioconazole per 100 kg of seed.

2. A method according to claim 1, wherein Prothioconazole is used in combination with at least one further agrochemically active compound.

3. A method according to claim 1, wherein the treating of the seed induces resistance against phytopathogenic pathogens or pests.

4. A method according to claim 1, wherein the treating of the seed induces resistance against abiotic stresses.

5. A method according to claim 1, wherein the treating of the seed induces expression of defense genes in the plant.

6. A method according to claim 1, wherein local or systemic acquired resistance (SAR), is induced.

7. A method according to claim 1, wherein systemic acquired resistance (SAR) is induced.

8. A method according to claim 1, wherein the treating of the seed induces resistance against phytopathogenic fungi, oomycetes, bacteria, viruses, viroids, *mycoplasma*-like organisms, protozoa, insects, acari or nematode.

9. A method according to claim 1, wherein the treating of the seed induces resistance against pathogens of fungal diseases.

10. A method according to claim 1, wherein the plant is oilseed rape.

11. A method according to claim 1, wherein the plant is wheat.

12. A method according to claim 1, wherein prothioconazole is the sole agrochemically active component used in the method.

13. A method according to claim 2, wherein the further agrochemically active compound is tebuconazole or fluopyram.

* * * * *